United States Patent
Van Kampen et al.

(10) Patent No.: US 9,055,874 B2
(45) Date of Patent: Jun. 16, 2015

(54) MOTION TRACKER TO DETECT AND CORRECT FOR MOVEMENT OF A PATIENT IN A CT SCANNER

(75) Inventors: William C. Van Kampen, Saline, MI (US); Predrag Sukovic, Birmingham, MI (US)

(73) Assignee: Xoran Technologies, Inc., Ann Arbor, MI (US)

( * ) Notice: Subject to any disclaimer, the term of this patent is extended or adjusted under 35 U.S.C. 154(b) by 1452 days.

(21) Appl. No.: 12/020,811

(22) Filed: Jan. 28, 2008

(65) Prior Publication Data

US 2008/0181358 A1  Jul. 31, 2008

Related U.S. Application Data

(60) Provisional application No. 60/897,568, filed on Jan. 27, 2007.

(51) Int. Cl.
| G01D 18/00 | (2006.01) |
| A61B 6/03 | (2006.01) |
| A61B 19/00 | (2006.01) |
| A61B 6/00 | (2006.01) |

(52) U.S. Cl.
CPC ............... *A61B 6/032* (2013.01); *A61B 19/203* (2013.01); *A61B 6/462* (2013.01); *A61B 6/527* (2013.01)

(58) Field of Classification Search
CPC ........ A61B 6/032; A61B 6/462; A61B 6/527; A61B 19/203; A61B 2019/5483; A61B 2019/5495

USPC ............ 378/4, 8, 20, 95, 163, 165, 206, 207; 600/426

See application file for complete search history.

(56) References Cited

U.S. PATENT DOCUMENTS

| 5,128,864 | A |  | 7/1992 | Waggener et al. |
| 5,954,647 | A | * | 9/1999 | Bova et al. ..................... 600/407 |
| 5,991,701 | A | * | 11/1999 | Triano .......................... 702/150 |
| 6,122,541 | A |  | 9/2000 | Cosman et al. |
| 2002/0015469 | A1 | * | 2/2002 | Oshima et al. .................. 378/15 |
| 2003/0152195 | A1 | * | 8/2003 | Hebecker et al. ............. 378/162 |
| 2004/0258210 | A1 | * | 12/2004 | Ritter ............................ 378/198 |
| 2007/0253541 | A1 | * | 11/2007 | Sukovic et al. ............... 378/205 |
| 2008/0031414 | A1 | * | 2/2008 | Coppens ......................... 378/65 |
| 2009/0022266 | A1 | * | 1/2009 | Stayman et al. .................. 378/8 |

* cited by examiner

*Primary Examiner* — Toan Ton
*Assistant Examiner* — Mona M Sanei
(74) *Attorney, Agent, or Firm* — Carlson, Gaskey & Olds, P.C.

(57) ABSTRACT

A motion tracker including a head band and laser devices that direct laser beams having non-concentric axes to a charge coupled device is used to determine movement of a patient during a CT scan. When the patient is motionless, the laser devices each direct a laser beam along a line, and the laser beams contact the charge coupled device at a contact location. If the patient moves, the laser devices, and therefore the contact locations, move. The charge coupled device detects the movement of the contact locations to determine the movement of the patient. A computer adjusts the x-ray image taken at the time of the movement to accommodate for this movement.

20 Claims, 5 Drawing Sheets

MOTION TRACKER TO DETECT AND CORRECT FOR MOVEMENT OF A PATIENT IN A CT SCANNER

REFERENCE TO RELATED APPLICATIONS

This application claims priority to U.S. Provisional Patent Application No. 60/897,568 filed Jan. 27, 2007.

BACKGROUND OF THE INVENTION

The present invention relates generally to a motion tracker that detects and corrects for movement of a patient in during a CT scan.

A CT scanner takes a plurality of x-ray images of a part of a patient to create a three dimensional CT image. During the CT scan, the patient must remain still. Any movement of the patient during the CT scan can negatively affect the resulting three dimensional CT image.

SUMMARY OF THE INVENTION

A motion tracker is used to determine movement of a patient during a CT scan. In one example, the motion tracker includes a head band that fits around a head of the patient and three laser devices that direct laser beams having non-concentric axes to a charge coupled device.

When the patient is motionless, the laser devices each direct a laser beam along a line, and the laser beams contact the charge coupled device at a contact location. If the patient moves, the laser devices, and therefore the contacts location, move. The charge coupled device detects the movement of the contact locations of the laser beams on the charge coupled device to determine the movement of the laser beams and therefore the patient.

If the charge coupled device detects movement of the patient, a computer adjusts the x-ray image taken at the time of the movement to accommodate for this movement. Therefore, any movement of the patient during the CT scan does not affect the final three dimensional CT image.

These and other features of the present invention will be best understood from the following specification and drawings.

DETAILED DESCRIPTION OF THE PREFERRED EMBODIMENT

Figure 1:
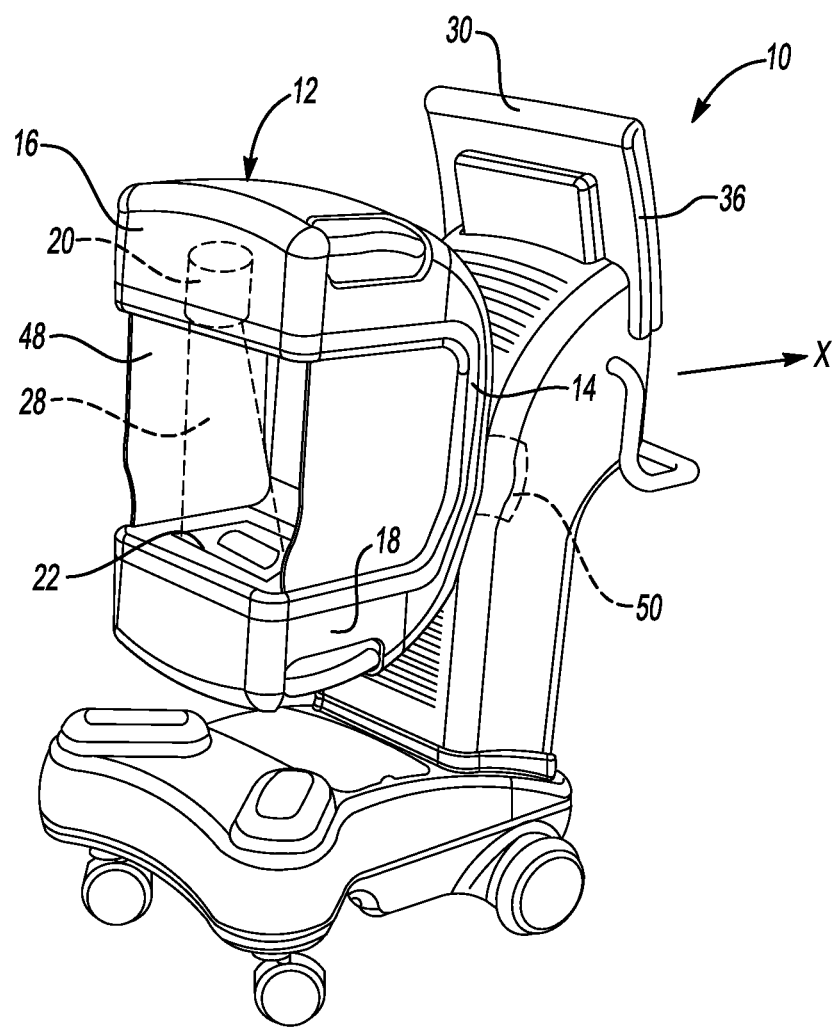
FIG. 1 schematically illustrates a first embodiment CT scanner.

FIG. 1 illustrates a CT scanner 10 of the present invention including a gantry 12 that supports and houses components of the CT scanner 10. In one example, the gantry 12 includes a cross-bar section 14, and a first arm 16 and a second arm 18 each extend substantially perpendicularly from opposing ends of the cross-bar section 14 to form the c-shaped gantry 12. The first arm 16 houses an x-ray source 20 that generate x-rays 28. In one example, the x-ray source 20 is a cone-beam x-ray source. The second arm 18 houses a complementary flat-panel detector 22. The x rays 28 are directed toward the detector 22 which includes a converter (not shown) that converts the x-rays 28 from the x-ray source 20 to visible light and an array of photodetectors behind the converter to create an image. As the gantry 12 rotates about the patient P, the detector 22 takes a plurality of x-ray images at a plurality of rotational positions. Various configurations and types of x-ray sources 20 and detectors 22 can be utilized, and the invention is largely independent of the specific technology used for the CT scanner 10.

Figure 2:
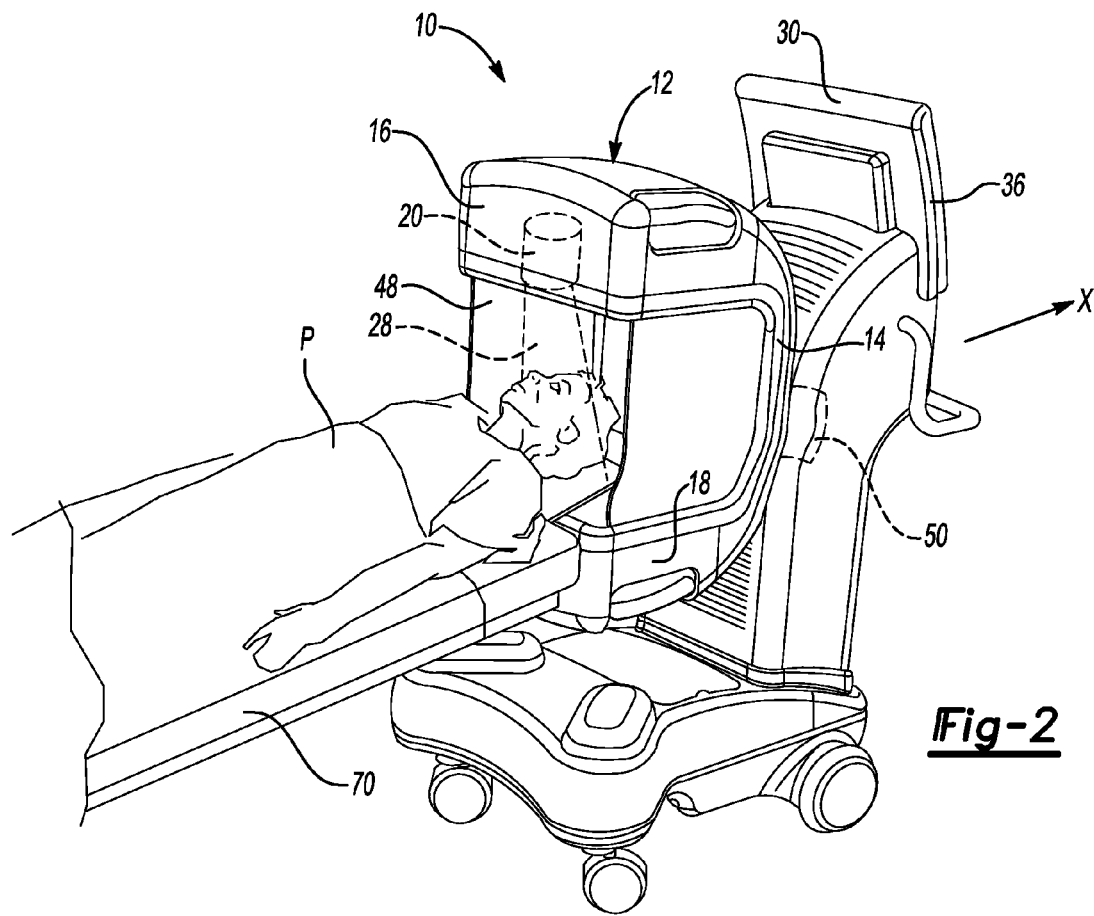
FIG. 2 illustrates the CT scanner of FIG. 1 with a part of a patient received in the CT scanner.
Figure 3:
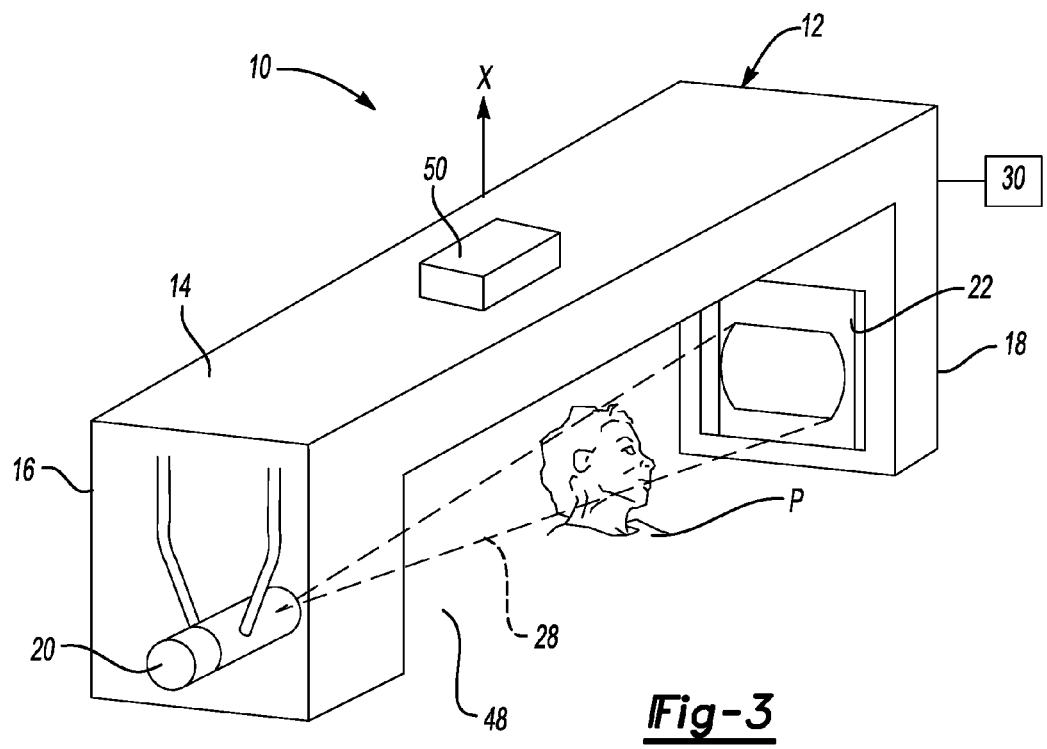
FIG. 3 illustrates a second embodiment of the CT scanner.

FIG. 2 illustrates the CT scanner 10 with a part of the patient P received in a space 48 between the first arm 16 and the second arm 18. A motor 50 rotates the gantry 12 about an axis of rotation X to obtain a plurality of x-ray images of the patient P at the plurality of rotational positions. The axis of rotation X is positioned between the x-ray source 20 and the detector 22. The gantry 12 can be rotated approximately slightly more than 360 degrees about the axis of rotation X. In one example, as shown in FIGS. 1 and 2, the axis of rotation X is substantially horizontal. In this example, the patient P is typically lying down on a table 70. Alternatively, as shown in FIG. 3, the axis of rotation X is substantially vertical. Typically, in this example, the patient P is sitting upright.

Figure 4:
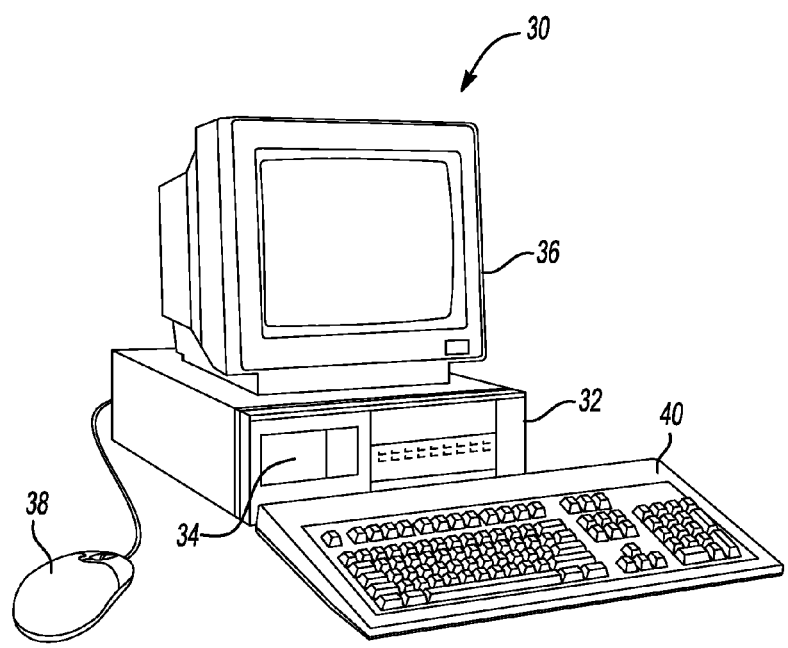
FIG. 4 illustrates a computer employed with the CT scanner.

As shown schematically in FIG. 4, the CT scanner 10 further includes a computer 30 having a microprocessor or CPU 32, a storage 34 (memory, hard drive, optical, and/or magnetic, etc), a display 36, a mouse 38, a keyboard 40 and other hardware and software for performing the functions described herein. The computer 30 powers and controls the x-ray source 20 and the motor 50. The plurality of x-ray images taken by the detector 22 are sent to the computer 30. The computer 30 generates a three-dimensional CT image from the plurality of x-ray images utilizing any known techniques and algorithms. The three-dimensional CT image is stored on the storage 34 of the computer 30 and can be displayed on the display 36 for viewing.

Figure 5:
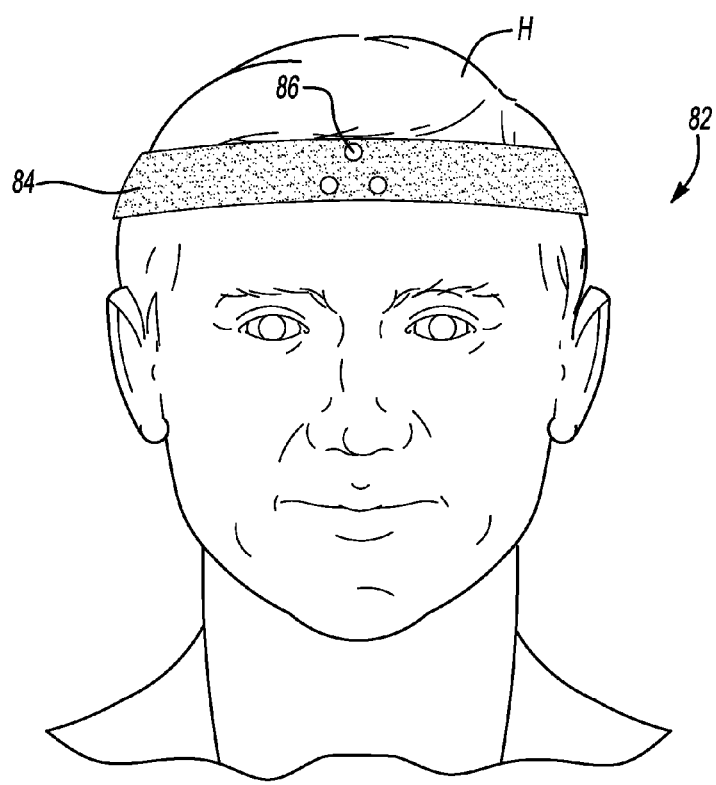
FIG. 5 illustrates a front view of a head holder attached to a head of the patient including at least one laser device.
Figure 6:
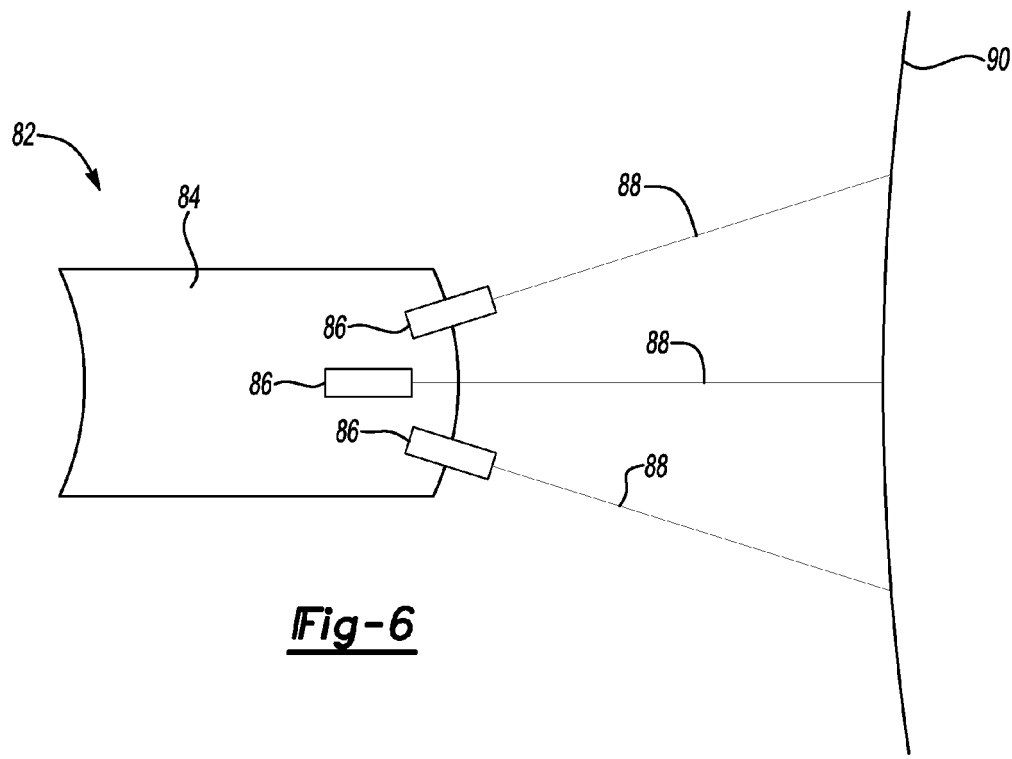
FIG. 6 illustrates a side view of the head holder including three laser devices.
Figure 7:
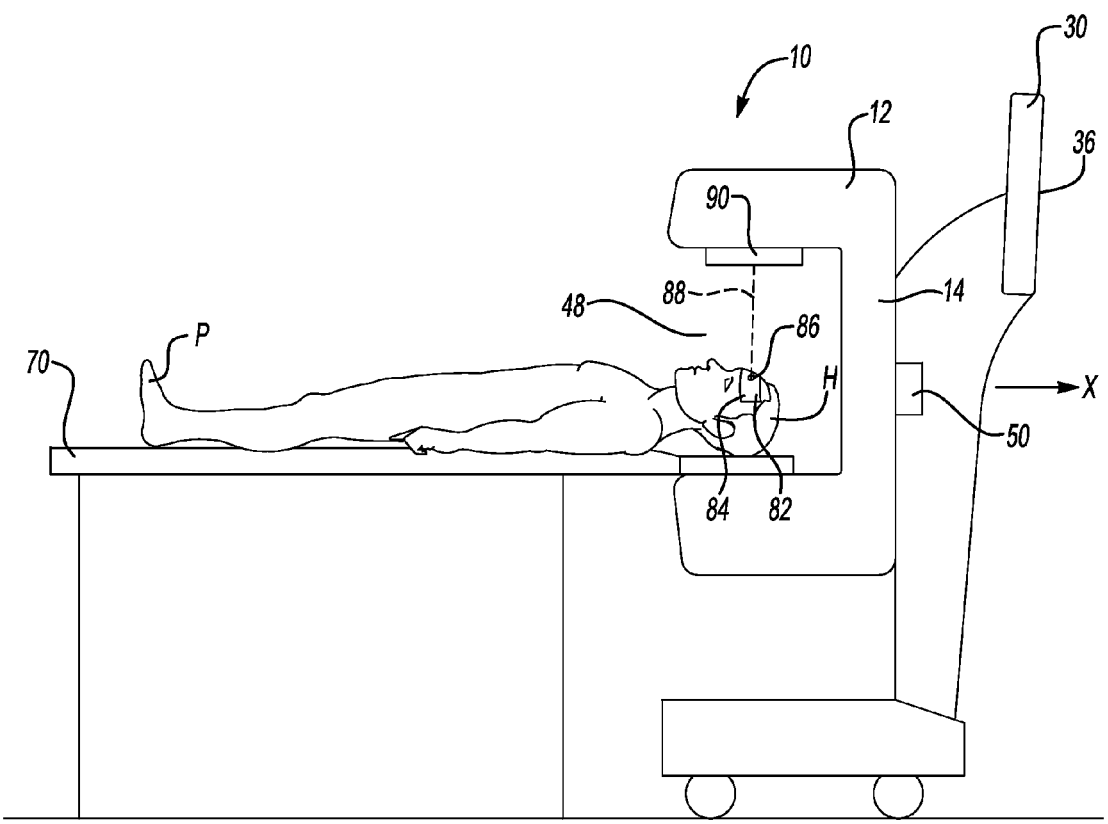
FIG. 7 illustrates a side view of the patient in a CT scanner wearing the head holder that directs laser beams towards a charge coupled device.

A motion tracker 82 is used to determine if the patient P moves during the CT scan. In one example shown in FIGS. 5 and 6, the motion tracker 82 includes a head band 84 that fits around a head H of the patient P. The motion tracker 82 includes at least one laser device 86 that shoots a laser beam 88. In one example, the motion tracker 82 includes three laser devices 86 that each direct a laser beam 88. All three laser beams 88 have non-concentric axes and are each directed to a contact location on a charge coupled device 90. The laser beams 88 form a cone shaped pattern to allow for multi-directional detection of movement of the patient P. As shown in FIG. 7, in one example, the charge coupled device 90 is located on the CT scanner 10, such as on a ceiling of the gantry 12 above the patient P when the patient P is lying on the table 70. However, the charge coupled device 90 can be located anywhere on the CT scanner 10 or in a room containing the CT scanner 10.

During the CT scan, the laser devices 86 each direct a laser beam 88 towards the charge coupled device 90, and the computer 30 detects movement of the patient P by determining the movement of the contact locations of the laser beams 88 on the charged coupled device 90. If it is determined that the patient P has moved too much during the CT scan, another CT scan may be necessary.

Figure 8:
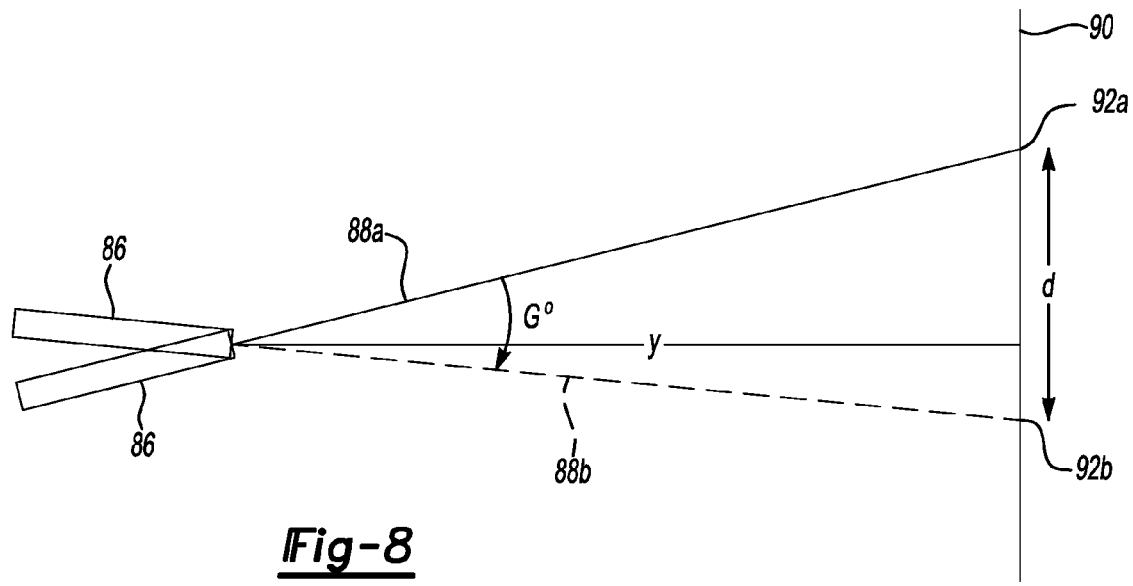
FIG. 8 illustrates a side view of one of the laser devices showing movement of on of the laser devices as the patient moves.

As shown in FIG. 8, when the patient P is motionless, each laser device 86 is positioned to direct the laser beam 88 along a line 88a towards a contact location 92a on the charge coupled device 90. If the patient P moves such that the laser device 86 is positioned to direct the laser beam 88 along a line 88b towards a contact location 92b on the charge coupled device 90, the charge coupled device 90 detects this movement, which is provided to the computer 30. The lines 88a and 88b are separated by an angle G°, and the locations 92a and 92b are separated by a distance d. Although the amount of movement of the laser device 86 appears minimal, the distance d between the lines 88a and 88b is greater at the charge coupled device 90 as the charged coupled device 90 is located at a distance y from the laser device 86.

A small amount of movement of a laser device 86 causes a relatively larger amount of movement of the contact locations 92a and 92b where the laser beams 88 contact the charge coupled device 90. As the angle G° between the lines 88a and 88b changes, the distance d between the lines 88a and 88b changes. The charge coupled device 90 detects the location 92 of the contact of the laser beam 88 on the charge coupled device 90, and the computer 30 determines the movement of the laser beams 88 and therefore the patient P.

The computer 30 uses the information detected by the charge coupled device 90 to correct for movement of the patient P during the CT scan. If the charge coupled device 90 detects movement of the patient P based on the contact locations 92 of the laser beams 88 on the charge coupled device 90, the computer 30 adjusts the x-ray image taken at the time of the movement to accommodate for this movement. Therefore, any movement of the patient P during the CT scan does not affect the final three dimensional CT image.

Figure 9:
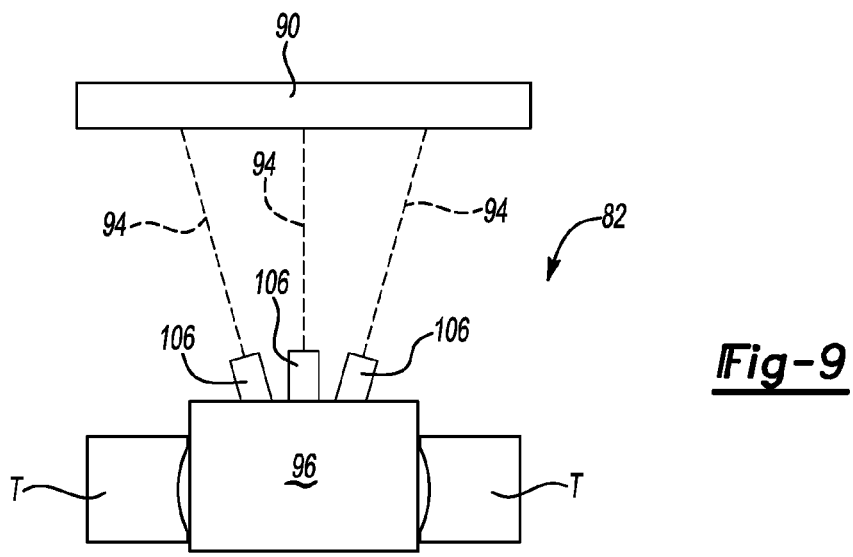
FIG. 9 illustrates a cross-sectional side view of a bite plate including at least one laser device.
Figure 10:
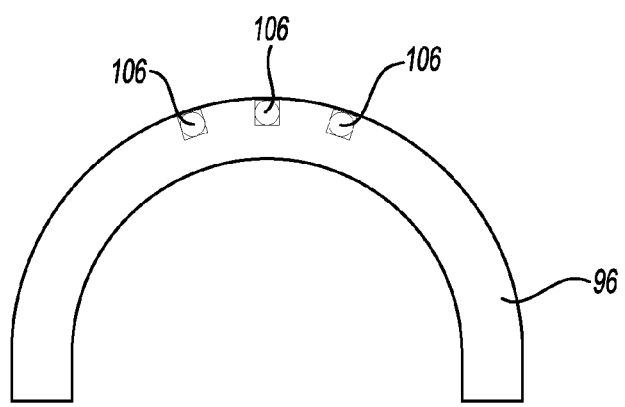
FIG. 10 illustrates a top view of the bite plate.

In another example shown in FIGS. 9 and 10, the motion tracker 82 is a bite plate 96 that is placed between the teeth T of the patient P. The bite plate 96 includes at least one laser device 106 that directs a laser beam 94 towards the charge coupled device 90. The charge coupled device 90 detects and corrects for movement of the patient P using the laser device 106 and the laser beams 94, which operate as described above.

The foregoing description is only exemplary of the principles of the invention. Many modifications and variations are possible in light of the above teachings. It is, therefore, to be understood that within the scope of the appended claims, the invention may be practiced otherwise than using the example embodiments which have been specifically described. For that reason the following claims should be studied to determine the true scope and content of this invention.

What is claimed is:

1. A motion tracker to determine motion of a patient during a CT scan, the motion tracker comprising:
    a component to be placed on a patient;
    at least one laser device on the component that directs a laser beam towards a sensor, wherein the sensor detects movement of the laser beam to determine if the patient has moved during the CT scan; and
    a computer that uses information detected by the sensor to correct for movement of the patient during the CT scan and adjusts an x-ray image taken at a time of the movement to accommodate for the movement of the patient.

2. The motion tracker as recited in claim 1 wherein the motion tracker comprises a head band that fits around a head of the patient.

3. The motion tracker as recited in claim 1 wherein the sensor is a charged coupled device.

4. The motion tracker as recited in claim 1 wherein the at least one laser device comprises three laser devices that each direct one of three laser beams, the three laser beams having non-concentric axes and each contacting the sensor at a contact point.

5. The motion tracker as recited in claim 4 wherein the three laser beams define a cone shape, allowing for multiple directional detection of movement of the patient.

6. The motion tracker as recited in claim 1 wherein the sensor is located on a gantry of a CT scanner.

7. The motion tracker as recited in claim 1 wherein the component is a bite plate placed between teeth of the patient.

8. The motion tracker as recited in claim 1 wherein the laser beam defines a line and is visible.

9. A CT scanner assembly comprising:
    a CT scanner including a gantry including a cross-bar section, a first arm and a second arm that each extend substantially perpendicularly to the cross-bar section, an x-ray source housed in the first arm to generate x-rays, an x-ray detector housed in the second arm and mounted opposite the x-ray source to obtain a plurality of x-ray images, and a sensor mounted to the gantry;
    a motion tracker to determine motion of a patient during a CT scan, the motion tracker including a component to be placed on the patient and at least one laser device on the component that directs a laser beam towards the sensor, wherein the sensor detects movement of the laser beam to determine if the patient has moved during the CT scan; and
    a computer that generates a three dimensional CT image from the plurality of x-ray images and uses information detected by the sensor to correct for movement of the patient during the CT scan and adjusts an x-ray image taken at a time of the movement to accommodate for the movement of the patient.

10. The CT scanner assembly as recited in claim 9 wherein the motion tracker comprises a head band that fits around a head of the patient.

11. The CT scanner assembly as recited in claim 9 wherein the sensor is a charged coupled device.

12. The CT scanner assembly as recited in claim 9 wherein the at least one laser device comprises three laser devices that each direct one of three laser beams, the three laser beams having non-concentric axes and each contacting the sensor at a contact point.

13. The CT scanner assembly as recited in claim 12 wherein the three laser beams define a cone shape, allowing for multiple directional detection of movement of the patient.

14. The CT scanner assembly as recited in claim 9 wherein the component is a bite plate placed between teeth of the patient.

15. The CT scanner system as recited in claim 9 wherein the laser beam defines a line and is visible.

16. A method to determine motion of a patient during a CT scan, the method comprising the steps of:
    placing a motion tracker on a patient;
    directing a laser beam from at least one laser device of the motion tracker to a sensor;

detecting movement of the laser beam with the sensor to determine movement of the patient;
obtaining a plurality of x-ray images of the patient;
obtaining information relating to movement of the laser beam; and
adjusting an x-ray image obtained at a time of movement based on the information to accommodate for the movement of the patient during the CT scan.

17. The method as recited in claim 16 wherein the step of directing the laser beam comprises directing three laser beams having non-concentric axes to the sensor.

18. The method as recited in claim 17 wherein the three laser beams define a cone shape, allowing for multiple directional detection of movement of the patient.

19. The method as recited in claim 16 further including the step of mounting the sensor on a gantry of a CT scanner.

20. The method as recited in claim 16 wherein the laser beam defines a line and is visible.

* * * * *